(12) United States Patent
Chuang

(10) Patent No.: US 8,226,420 B2
(45) Date of Patent: Jul. 24, 2012

(54) WRIST WORN ELECTRONIC DEVICE WITH BELT EMBEDDED WITH SENSOR

(75) Inventor: Ping-Yang Chuang, Taipei Hsien (TW)

(73) Assignee: Hon Hai Precision Industry Co., Ltd., Tu-Cheng, New Taipei (TW)

( * ) Notice: Subject to any disclaimer, the term of this patent is extended or adjusted under 35 U.S.C. 154(b) by 0 days.

(21) Appl. No.: 12/959,293

(22) Filed: Dec. 2, 2010

(65) Prior Publication Data
US 2012/0028479 A1    Feb. 2, 2012

(30) Foreign Application Priority Data
Jul. 29, 2010    (TW) ................................ 99125200 A

(51) Int. Cl.
*H01R 33/00*    (2006.01)
(52) U.S. Cl. ........................................... 439/37; 439/38

(58) Field of Classification Search ............... 439/37–39
See application file for complete search history.

(56) References Cited

U.S. PATENT DOCUMENTS

| 5,158,473 | A  | * | 10/1992 | Takahashi et al. | ............. | 439/353 |
| 7,658,613 | B1 | * | 2/2010 | Griffin et al. | ................... | 439/39 |
| 2007/0072442 | A1 | * | 3/2007 | DiFonzo et al. | ................ | 439/39 |
| 2010/0267250 | A1 | * | 10/2010 | Schiff et al. | ..................... | 439/39 |

* cited by examiner

*Primary Examiner* — Tulsidas C Patel
*Assistant Examiner* — Travis Chambers
(74) *Attorney, Agent, or Firm* — Altis Law Group, Inc.

(57) ABSTRACT

A wrist worn electronic device includes a main body having a processor and a receiving member electrically connected to the processor. A belt includes an electronic component and a connection member electrically connected to the electronic component. The connection member is used to engage the receiving member, to connect the belt to the main body and electrically connect the electronic component to the processor.

5 Claims, 3 Drawing Sheets

WRIST WORN ELECTRONIC DEVICE WITH BELT EMBEDDED WITH SENSOR

BACKGROUND

1. Technical Field

The present disclosure relates to wrist worn electronic devices and, particularly, to a wrist worn electronic device having a belt embedded with an electronic component.

2. Description of Related Art

A wrist worn electronic device such as an electronic watch having a sensor is commonly known. The sensor is mounted on a watch case or on a shield for shielding a dial, so that the sensor is projected from the surface of the shield or the watch case. In certain circumstance, it may be preferable that the sensor be mounted within a belt of the watch. So it would be convenient if a belt with an embedded sensor could be automatically and electrically connected to a controller in a watch body when the belt is connected to the watch body.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

Embodiments of the present disclosure will now be described in detail below, with reference to the accompanying drawings.

Figure 1:
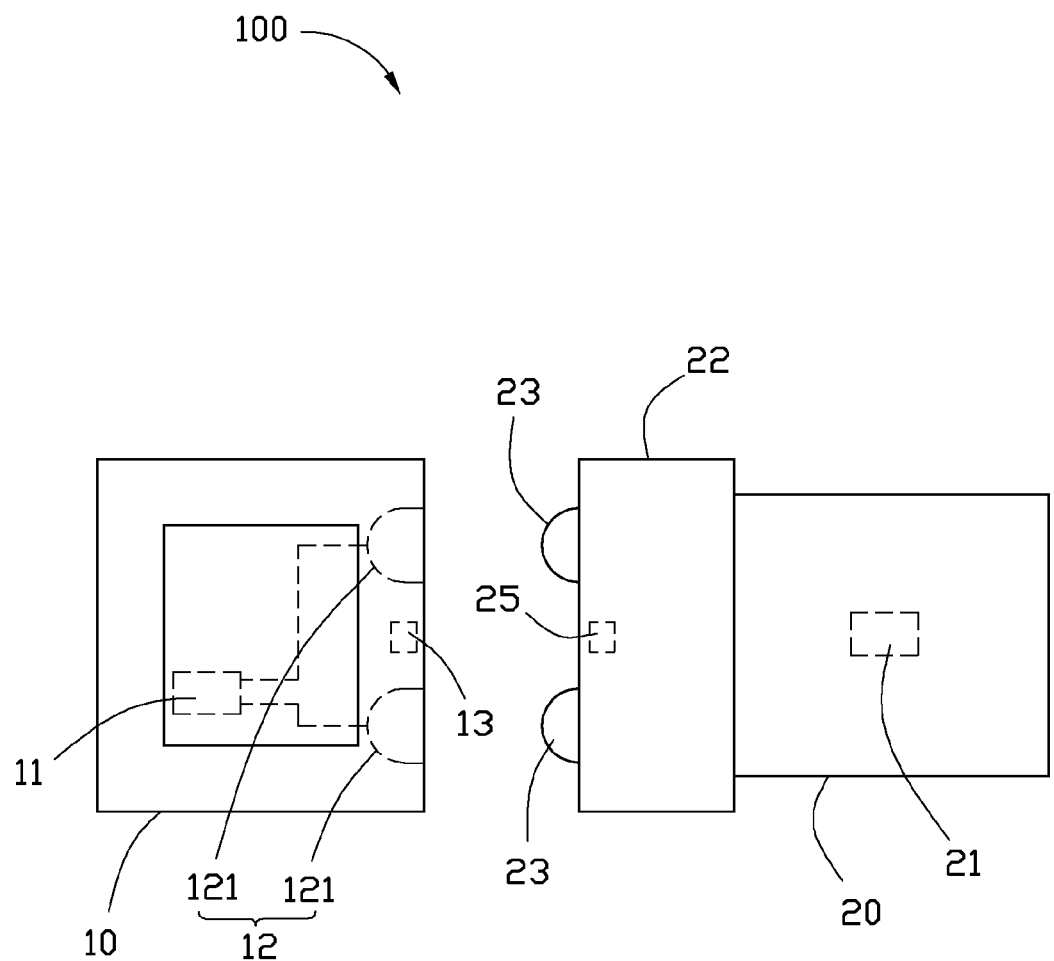
FIG. 1 is a schematic planar view of a wrist worn electronic device in accordance with one embodiment.
Figure 2:
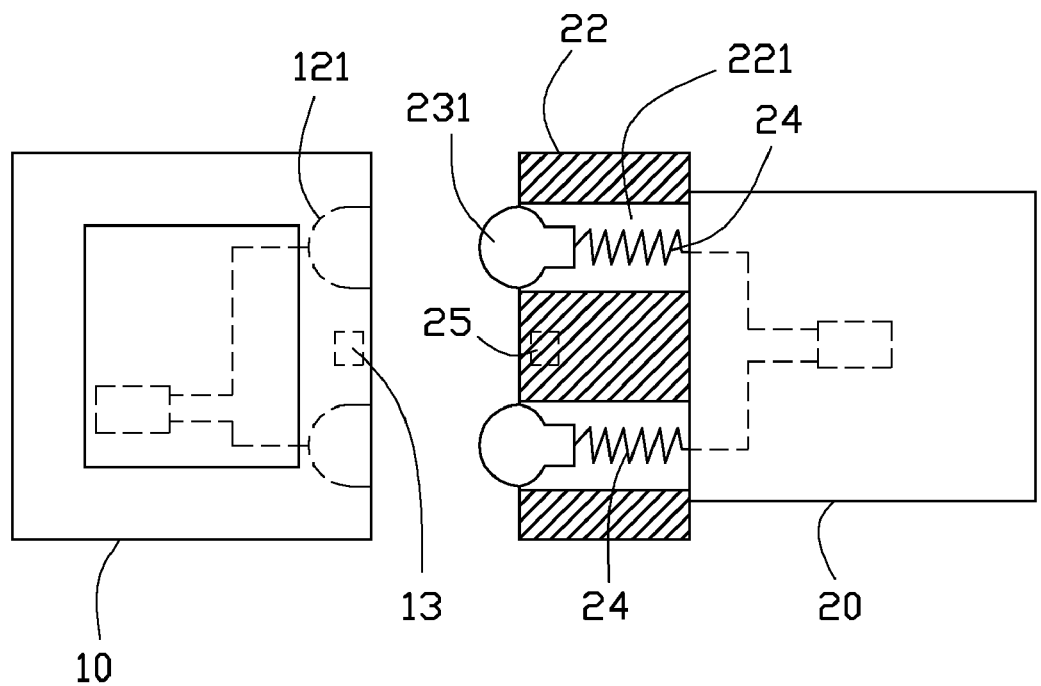
FIG. 2 is similar to FIG. 1 but with one portion presented in a cross-sectional view.

Referring to FIGS. 1 and 2, a wrist worn electronic device 100 includes a main body 10 and a belt 20. The main body 10 includes a processor 11. The belt 20 includes an electronic component 21 embedded therein. In the embodiment, the electronic component 21 may be a temperature sensor, a gyro sensor, etc. The belt 20 can be made of soft material, such as rubber.

The main body 10 includes a receiving member 12 electrically connected to the processor 11. In the embodiment, the receiving member 12 is in the form of two cavities 121 formed in one side of the main body 10. Each cavity 121 is coated with a conductive layer that is electrically connected to the processor 11.

The belt 20 also includes a connection block 22 at its end and two connection members 23. The connection block 22 defines two receiving holes 221 to receive the connection members 23. Each connection member 23 includes a spherical head 231. The head 231 is slightly greater than the cavity 121, and can be tightly received in the cavity 121, allowing the electronic component 21 to be electrically connected to the processor 11.

In the embodiment, a spring 24 is received in one receiving hole 221 connected to one end of each connection member 23. The spring 24 is used to apply a pushing force to the connection member 23, to cause the head 231 to be tightly received in the cavity 121.

In the embodiment, a magnet 13 is embedded in the main body 10 adjacent to the side defining the cavities 121. A magnet 25 is embedded in the connection block 22. The magnets 13 and 25 attract each other, which assist to strengthen connections between the main body and the belt.

Figure 3:
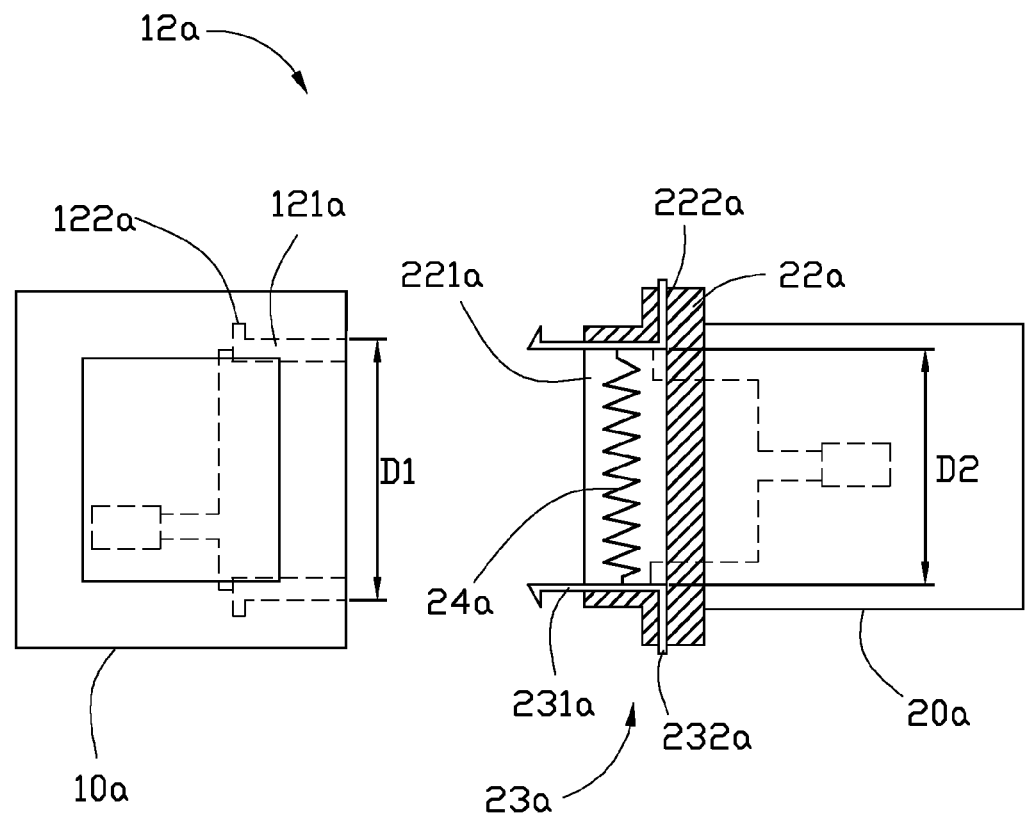
FIG. 3 is similar to FIG. 2, but in accordance with an alternative embodiment.

Referring to FIG. 3, in an alternative embodiment, a connection block 22a defines an open-ended receiving chamber 221a and two slots 222a communicating with the chamber 221a. A connection member 23a includes two hooked shanks 231a, and two handles 232a respectively protruding from an opposite end of each shank 231a. The shanks 231a are partly received in the chamber 221a, with their hooks protruding out of the chamber 221a. A spring 24a is received in the chamber 221a and includes two ends respectively connected to the two shanks 231a. Each handle 232a is partly received in one slot 222a and includes an end external to the connection block 22a.

A receiving member 12a defines two blind holes 121a each defining a dent 122a in its lateral surface. To connect the belt 20a to the main body 10a, the handles 232a can be depressed to move the shanks 231a toward each other, until the shanks 231a are aligned with the blind holes 121a. The connection block 22a can then pushed to cause the shanks 231a to slide into the blind holes 121a. After the shanks 231a resist against the ends of the blind holes 121a, the handles 232a can be released. The spring 24a then pushes the shanks 231a to move away from each other, ultimately causing the hook of each shank 231 a to be received in the corresponding dent 122a, which connects the belt 20a to the main body 10a.

While various embodiments have been described and illustrated, the disclosure is not to be constructed as being limited thereto. Various modifications can be made to the embodiments by those skilled in the art without departing from the true spirit and scope of the disclosure as defined by the appended claims.

What is claimed is:

1. A wrist worn electronic device comprising:
    a main body comprising a processor and a receiving member electrically connected to the processor, wherein the receiving member comprises two blind holes each defining a dent in a lateral surface thereof; and
    a belt comprising an electronic component, two connection members electrically connected to the electronic component, a connection block defining an open-ended receiving chamber and two slots communicating with the chamber, and a spring, wherein each connection member comprises a shank partly received in the chamber and having a hook at an end thereof, and a handle protruding from an opposite end of the shank and partly received in one of the slot, the hook of each shank protrudes out of the chamber and is able to be received in one of the dents to connect the belt to the main body, and the spring connects the two shanks and is configured to apply a push force to the two shanks.

2. The wrist worn electronic device according to claim 1, wherein the main body comprises a first magnet, the belt comprises a second magnet, the first magnet and the second magnet attract each other to assist to strengthen connections between the main body and the belt.

3. The wrist worn electronic device according to claim 1, wherein the receiving member comprises two cavities defined in the main body, each of the two cavities comprises a conductive layer coated thereon, the connection member comprises two conductive heads that are able to be fitted into the two cavities.

4. The wrist worn electronic device according to claim 3, wherein each of the conductive heads is spherical.

5. The wrist worn electronic device according to claim 3, wherein the belt further comprises two spring members, two ends of each of the spring members are respectively connected to the processor and one of the two conductive heads, the spring members are configured to apply a spring pushing force to the two conductive heads, to cause the two conductive heads to be tightly received in the two cavities.

* * * * *